(12) United States Patent
Peretto et al.

(10) Patent No.: US 8,574,163 B2
(45) Date of Patent: Nov. 5, 2013

(54) APPARATUS AND METHOD FOR A NONINVASIVE ESTIMATE OF THE CHARACTERISTICS OF A PERIODIC/CYCLIC BODILY SOUND IN A REGION CLOSE TO ITS SOURCE

(75) Inventors: Lorenzo Peretto, Fratta Polesine (IT); Luca Longhini, Ferrara (IT)

(73) Assignee: Luca Longhini, Ferrara (IT)

( * ) Notice: Subject to any disclaimer, the term of this patent is extended or adjusted under 35 U.S.C. 154(b) by 2070 days.

(21) Appl. No.: 11/595,451

(22) Filed: Nov. 9, 2006

(65) Prior Publication Data

US 2007/0106180 A1    May 10, 2007

Related U.S. Application Data

(60) Provisional application No. 60/734,774, filed on Nov. 9, 2005.

(51) Int. Cl.
*A61B 7/04* (2006.01)
(52) U.S. Cl.
USPC ........................................................ 600/528
(58) Field of Classification Search
USPC .................................... 600/528, 438, 485
See application file for complete search history.

(56) References Cited

U.S. PATENT DOCUMENTS

| | | | | |
|---|---|---|---|---|
| 4,528,689 | A * | 7/1985 | Katz | 381/67 |
| 5,492,129 | A | 2/1996 | Greenberger | |
| 5,680,868 | A * | 10/1997 | Kahn et al. | 600/494 |
| 6,050,950 | A | 4/2000 | Mohler | |
| 6,368,283 | B1 * | 4/2002 | Xu et al. | 600/485 |
| 2002/0042574 | A1 * | 4/2002 | Manor et al. | 600/454 |

FOREIGN PATENT DOCUMENTS

EP    0 536 548    4/1993

OTHER PUBLICATIONS

A New Noninvasive Method for Estimation of Pulmonary Arterial Pressure in Mitral Stenosis; by: Carlo Longhini, et al.; The American Journal of Cardiology vol. 68, (Aug. 1, 1991) pp. 398-401.
A new, simple, and accurate method for non-invasive estimation of pulmonary arterial pressure; J. Xu et al.; www.hearjnl.com, (Heart 2002) vol. 88; pp. 76-80.
Noninvasive Estimation of the Pulmonary Systolic Pressure From the Spectral Analysis of the Second Heart Sound; S. Aggio et al.; Acta Cardiologica, vol. XLV, 1990, 3 pp. 199-202.
Estimation of Pulmonary Artery Pressure by Spectral Analysis of the Second Heart Sound; Danmin Chen et al.; The American Journal of Cardiology, vol. 78, (Oct. 1, 1996) pp. 785-789.
International Search Report dated Apr. 18, 2007.

* cited by examiner

*Primary Examiner* — Christopher D Koharski
*Assistant Examiner* — Michael Carey
(74) *Attorney, Agent, or Firm* — RatnerPrestia

(57) ABSTRACT

Methods and apparatus for noninvasively determining a sound pressure of a source that transmits a generally periodic acoustic signal including at least one signal component to a surface of a body are provided. The signal component at the surface of the body is received and an initial phase-inverted signal component is estimated responsive to the received signal component. The phase-inverted signal component, advanced by a predetermined time increment, is transmitted toward the source via the surface. The predetermined time increment corresponds to a distance of the signal component within the body. At least one feature of the transmitted signal component is adjusted until a further received signal approximates a minimum value. The adjusted signal component corresponds to the signal component at the distance. The apparatus determines the phase-inverted signal component that corresponds to the signal component being proximate to the source.

10 Claims, 7 Drawing Sheets

APPARATUS AND METHOD FOR A NONINVASIVE ESTIMATE OF THE CHARACTERISTICS OF A PERIODIC/CYCLIC BODILY SOUND IN A REGION CLOSE TO ITS SOURCE

CROSS REFERENCE TO RELATED APPLICATIONS

This application is related to and claims the benefit of U.S. Provisional Application No. US60/734,774 entitled NONINVASIVE APPARATUS FOR THE PULMONARY ARTERY PRESSURE MEASUREMENT filed on Nov. 9, 2005, the contents of which are incorporated herein by reference.

FIELD OF THE INVENTION

The present invention relates to the field of clinical evaluation of cardiac diseases and, more particularly, to methods and apparatus for noninvasively determining a sound pressure of a source located inside a body that transmits a generally periodic acoustic signal including a signal component to a surface of the body.

BACKGROUND OF THE INVENTION

Blood pressure measurements are known in the art and have been used for a number of years to aid in the diagnosis of cardiac and pulmonary diseases. In order to detect blood pressure, particularly at a position close to the source, systems that include invasive procedures such as vascular catheter-based systems (e.g. Swan-Ganz catheter) are typically used. Estimation of blood pressure may also be obtained through a noninvasive procedure, for example, using Doppler Echocardiography, in order to estimate cardiac pressures via known-in-the-art ultrasound techniques. In addition, methods using heart sounds analysis have also been proposed. For example, see U.S. Pat. No. 6,368,283 to Xu et al., entitled "Method and apparatus for estimating systolic and mean pulmonary artery pressures of a patient."

Invasive procedures, however, are typically uncomfortable for the patient. Vascular catheterization, for example, even in skilled hands, may carry various risks and complications. Conventional invasive procedures typically require highly skilled personnel (i.e. physicians or technicians) as well as the utilization of expensive equipment. Cardiac catheterization may also require use of a suitably equipped operating room, with attending operating room personnel.

SUMMARY OF THE INVENTION

The present invention is embodied in a method and a system for noninvasively determining a sound pressure of a source located inside of a body. The source transmits a generally periodic acoustic signal including at least one signal component to a surface of the body. The method includes the steps of a) receiving the signal component at the surface of the body and b) estimating an initial phase-inverted signal component responsive to the signal component received at the surface. The phase-inverted signal component approximates a phase-inverted version of the received signal component. The method further includes the step of c) transmitting the phase-inverted signal component advanced by a predetermined time increment toward the source via the surface. The predetermined time increment corresponds to a distance of the signal component within the body. The method further includes the steps of d) adjusting at least one feature of the transmitted signal component until a further received signal approximates a minimum value, e) setting the adjusted signal component determined in step d) as the phase-inverted signal component corresponding to the signal component at the distance and f) repeating steps c)-e) until the phase-inverted signal component corresponds to the signal component proximate to the source.

The present invention is further embodied in apparatus for noninvasively determining a sound pressure of a source located inside of a body. The source transmits a generally periodic acoustic signal including at least one signal component to a surface of the body. The apparatus includes a first acoustic transducer disposed on the surface for receiving the signal component at the surface of the body, a second acoustic transducer disposed on the surface of the body and a source pressure determination system. The source pressure determination system includes a signal generator configured to generate an estimated phase-inverted signal component responsive to the signal component received at the surface by the first acoustic transducer. The phase-inverted signal component approximates a phase-inverted version of the received signal component. The source pressure determination system further includes a controller for providing a predetermined time increment to the signal generator for advancing the generated phase-inverted signal component where the predetermined time increment corresponds to a distance of the signal component within the body. The second acoustic transducer transmits the advanced phase-inverted signal component provided by the signal generator toward the source. The controller further adjusts at least one feature of the estimated phase-inverted signal generated by the signal generator until a further signal received from the first acoustic transducer approximates a minimum value. The controller sets the adjusted signal component as the phase-inverted signal component corresponding to the signal component at the distance. The source pressure determination system determines the phase-inverted signal component that corresponds to the signal component being proximate to the source.

BRIEF DESCRIPTION OF THE DRAWINGS

The invention is best understood from the following detailed description when read in connection with the accompanying drawings. It is emphasized that, according to common practice, various features/elements of the drawings may not be drawn to scale. On the contrary, the dimensions of the various features/elements may be arbitrarily expanded or reduced for clarity. Moreover in the drawings, common numerical references are used to represent like features/elements. Included in the drawing are the following figures.

DETAILED DESCRIPTION OF THE INVENTION

Figure 1:
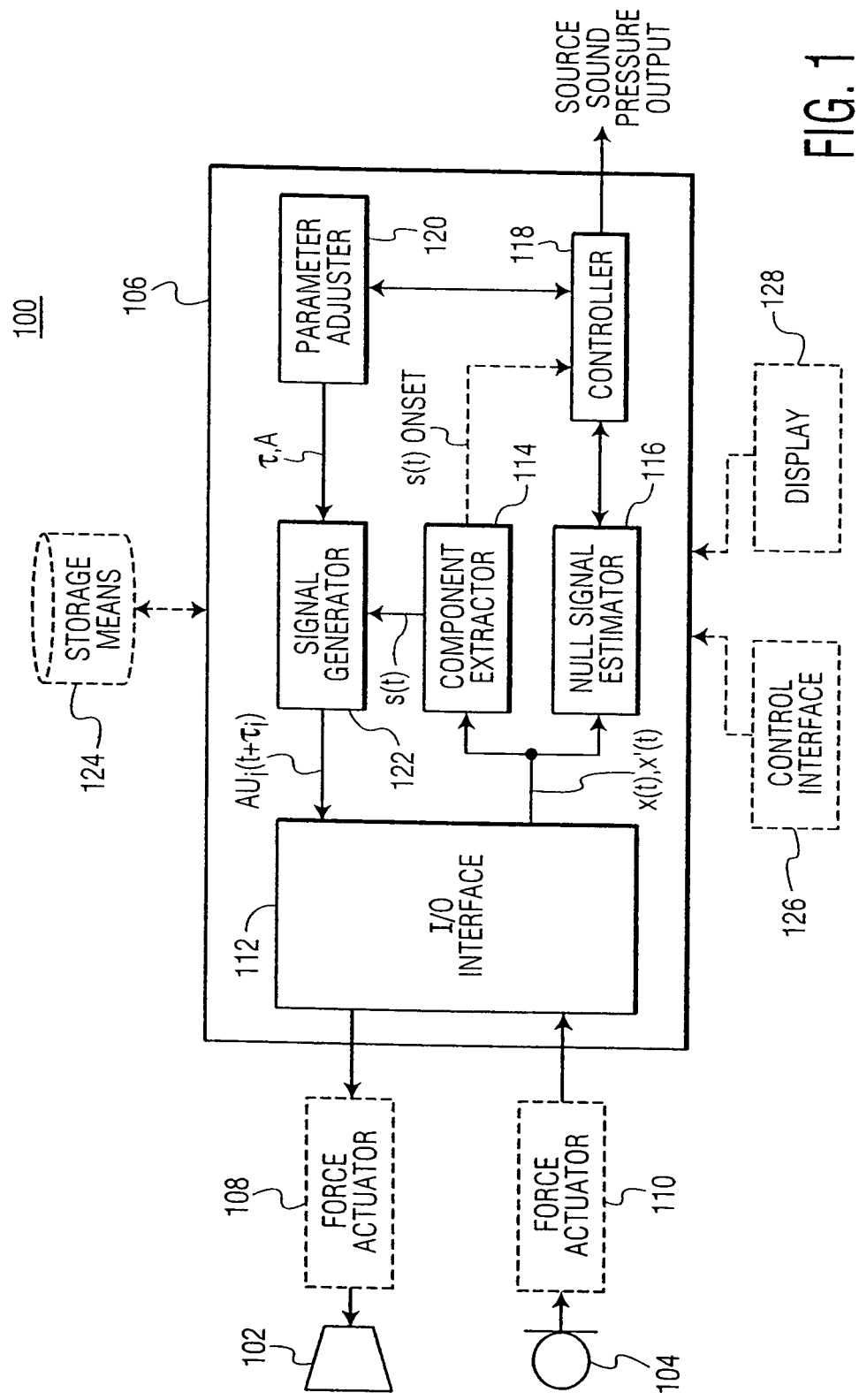
FIG. 1 is a functional block diagram illustrating an exemplary apparatus for noninvasively determining a source sound pressure according to an embodiment of the present invention.

The present invention may be embodied in apparatus and methods for noninvasively determining a sound pressure of a source that is located inside of a body and that transmits a generally periodic acoustic signal x(t) including at least one signal component s(t) to the skin surface. For example, the source may be a heart that transmits a heart sound signal including periodically generated first heart sounds (S1) and second heart sounds (S2). According to an exemplary embodiment of the present invention, the characteristics of the signal component may be estimated as if the signal component were acquired proximate to the source by using a phase-inverted version of the signal component received at the skin surface. For example, a signal component may include the sound emitted during the closure of one or more of a cardiac pulmonary valve, an aortic valve, a mitralic valve or a tricuspid valve of the heart. In particular, the characteristics may include the amplitude of the sound pressure wave (and the intensity) that is generated proximate to the source during the closure of one or more of the heart valves. These characteristics may be used to determine physiologic characteristics for a patient, for example, a blood pressure. The characteristics determined according to an exemplary embodiment of the present invention may be used to study various cardiovascular diseases. Although the present invention describes apparatus and methods related to determining a sound pressure for cardiac signals, it is contemplated that the present invention may be used to determine desired characteristics for any organ that produces a generally periodic acoustic signal including a desired signal component.

According to an exemplary embodiment of the present invention, an initial phase-inverted signal component $U_1(t)$ may be estimated from the signal component s(t) that has propagated to and is received at the skin surface. The initial estimated phase-inverted signal component $U_1(t)$ thus corresponds to the signal component s(t) received at the skin surface. The estimated phase-inverted signal may be transmitted toward the source from the skin surface, advanced by a predetermined time interval, in order to be combined with the signal component located at a distance within the body. At least one feature of the transmitted signal component may be adjusted until a received signal x'(t) approximates a minimum value. Accordingly, the signal x'(t) received at the skin surface may represent a null signal formed by the combination of the transmitted signal component and the signal component located at the distance within the body. The inverted signal used to produce the null signal may indicate an estimate of the phase-inverted signal component at this distance within the body. The process of transmitting an advanced estimated phase-inverted signal component and adjusting at least one feature of the transmitted signal component may be repeated until the phase-inverted signal corresponds to the signal component proximate to the source.

FIG. 1 is a functional block diagram illustrating an exemplary apparatus 100 for noninvasively determining a source sound pressure according to an embodiment of the present invention. A sound transmitter 102 receives and transmits a phase-inverted signal component $U_i(t)$, that may be advanced and amplitude adjusted, from sound pressure determination system 106, where i represents a sample index for advancing the phase-inverted signal component within the body (not shown) and i=0 to N. $U_i(t)$ at index i=0 represents an inverted extracted signal component from the received signal component at the skin surface (described further below). $U_i(t)$ at index i=N represents the estimated phase-inverted signal component proximate to the source. A sound receiver 104 receives the generally periodic acoustic signal x(t) including at least one signal component s(t) from a skin surface (not shown) and provides x(t) to sound pressure determination system 106. Sound pressure determination system 106 desirably generates the initial estimated phase-inverted signal component at the skin surface, $U_1(t)$, and subsequently $U_N(t)$ proximate to the source by adjusting at least one feature of the transmitted signal component (described further below).

It is understood that the value of N may depend upon the distance between the source and the skin surface and that this distance may vary for each person. It is contemplated that N may be about 10 or less. In accordance with an exemplary embodiment of the present invention, it is contemplated that the estimated phase-inverted signal may be determined to within about 1 to 3 cm from the source.

Sound transmitter 102 may be any acoustic transducer capable of transmitting the phase-inverted signal such that the transmitted signal maintains a linearity in a desired bandwidth and has an output power capable of providing suitable amplification over a desired amplitude adjusting range for $U_i(t)$. Sound receiver 104 may be any acoustic transducer capable of receiving an acoustic signal and maintaining a linearity in the desired bandwidth. In an exemplary embodiment, the desired bandwidth for the sound receiver 104 and sound transmitter 102 is between about 3 to 6 kHz. It is understood that a desired bandwidth may be determined according to the signal component of interest. It is contemplated that a force actuator 108 may be provided to measure a pressure applied to a skin surface (not shown) by sound transmitter 102. In addition, a force actuator 110 may be provided to measure a pressure applied to the skin surface by sound receiver 104. It is contemplated that any suitable force actuator for regulating a desired applied pressure to the skin surface may be used.

Sound pressure determination system 106 may be any system capable of acquiring an analog signal, processing the analog signal and providing an analog output signal. It is contemplated that sound pressure determination system 106 may include any computer having a processor (e.g. a digital signal processor) for generating and transmitting a phase-inverted signal component and determining a source sound pressure from the received signal using an algorithm in accordance with the subject invention. The sound pressure determination system 106 may include electronic components and any software suitable for performing at least part of the functions of generating the phase-inverted signal component and determining the source sound pressure.

Sound pressure determination system 106 includes an input/output (I/O) interface 112 for acquiring an analog signal from sound receiver 104 and providing an analog output signal to sound transmitter 102. Although not shown, I/O interface 112 may be configured to receive an electrocardiogram (ECG) signal in order to extract the desired signal component s(t) from the received signal x(t) (described further below). It is understood that I/O interface 112 may be any suitable interface capable of acquiring an analog signal x(t) and transmitting an analog signal $U_i(t)$ may be used. According to the components of sound pressure determination system 106, I/O interface 112 may also include known-in-the art analog to digital (A/D) and digital to analog (D/A) interfaces.

Sound pressure determination system 106 further includes a component extractor 114 for extracting the desired signal component s(t) from the received acoustic signal x(t). It is contemplated that any known-in-the-art method may be used to extract the signal component s(t) from the received signal x(t). For example, the signal component can be extracted directly from the received signal x(t) provided by the sound receiver 104 or the signal component s(t) may be extracted by using an ECG signal measured synchronously with the acoustic signal x(t). For example, as is known to the skilled person, two consecutive QRS complexes may be identified in the ECG signal and used to provide a timing window for extracting an S2 signal from x(t).

Sound pressure determination system 106 further includes a signal generator 122 for receiving the extracted signal component s(t) from component extractor 114 and generating a phase-inverted signal component, i.e. $U_0(t)=-s(t)$. Generally, signal generator 122 is responsive to a predetermined time increment $\tau_i$ and at least an amplitude A provided by parameter adjuster 120 in order to advance $U_i(t)$ according to time increment $\tau_i$ adjusted by amplitude A, such that $AU_i(t+\tau_i)$ is transmitted $\tau_i$ by sound transmitter 102. The process of advancing signal $U_i(t)$ in time and adjusting the amplitude A so that the transmitted phase-inverted signal reaches the signal component at a distance within the body is described further below.

The body may represent a transmission channel. Accordingly, as $U_i(t)$ propagates from the surface toward the source in the transmission channel, the amplitude may be attenuated due to the characteristics of the transmission channel. The transmission channel may also cause $U_i(t)$ to spread in the time domain and/or act as a filter to filter frequency components of $U_i(t)$ in the frequency domain.

According to an exemplary embodiment of the present invention, when the phase-inverted signal component $AU_i(t+\tau_i)$ is transmitted into the body via sound transmitter 102 and the amplitude A at the surface corresponds to the amplitude of signal component s(t) within the body, i.e. at a location corresponding to $\tau_i$, the transmitted signal will be combined with the signal component s(t). Because the transmission channel may attenuate $U_i(t)$, it is understood that the amplitude A may be adjusted to compensate for the attenuation of the transmission channel. Because $AU_i(t+\tau_i)$ is a phase-inverted signal, the combined signal x'(t) of the transmitted signal and the signal component may produce a null signal, i.e. a combined signal that approximates a minimum value. The signal x'(t) received from sound receiver 104, at an appropriate delay, may be the null signal representing the minimum value. Accordingly, $AU_i(t+\tau_i)$ may be determined to estimate the signal component with the appropriate amplitude at a location within the body. It is contemplated that $U_i(t)$ may also be adjusted to compensate for other time and/or frequency domain effects of the transmission channel.

Sound pressure determination system 106 includes a null signal estimator 116 configured to receive the combined signal x'(t) from sound receiver 104, i.e. the transmitted signal component $AU_i(t+\tau_i)$ combined with the signal component s(t). Null signal estimator 116 determines a value of the combined signal x'(t) and provides the result to controller 118. In an exemplary embodiment, null signal estimator 116 provides an integrated squared measure of the received signal x'(t) as the determined value.

Controller 118 is configured to receive the value of the x'(t) from null signal estimator 116 and to adjust at least the amplitude of the phase-inverted signal generated by signal generator 122 until controller 118 determines that the value of x'(t) received from null signal estimator 116 is the minimum value. Controller 118 is also configured to update the time index when the controller 118 determines that a minimum value is approximated. The time index is updated in order to advance the point at which the phase-inverted signal from the skin surface combines with the signal provided by the source to be proximate the source. Controller 118 may receive a signal component onset time from component extractor 114 in order to provide an appropriate time window for null signal generator 116 to determine a minimum value from the combined signal x'(t). that Null signal extractor 116, controller 118, parameter adjuster 120.

Controller 118 controls parameter adjuster 120 to provide the predetermined time increment $\tau_i$ and at least the amplitude parameter selected by controller 118 to signal generator 122. In an exemplary embodiment, the predetermined time increments are regularly spaced, for example, between about 100 µs to 1 ms. It is contemplated, however, that the predetermined time intervals may be irregularly spaced. For example, the predetermined time intervals may be more finely spaced as the source is approached in order to more accurately locate the source. It is further contemplated that the predetermined time intervals may include a first set of time intervals and a second set of time intervals. The first set of time intervals may provide a coarse location relative to the source. The second set of time intervals may be used to determine a more precise amplitude closer to the source.

It is contemplated that parameter adjuster 120 may also include other signal parameters, for example, a time-domain signal spreading parameter and a frequency domain filtering parameter to compensate the estimated phase-inverted signal for predetermined transmission channel effects in time and/or in frequency on the transmitted signal.

Apparatus 100 may optionally include storage means 124 for storing, for example, sound transmitter and/or sound receiver inverse filters, sets of predetermined time increments according to patient characteristics, time spreading compensation and/or frequency domain filtering due to patient characteristics corresponding to transmission channel characteristics. It is contemplated that different inverse filters may be stored that correspond to different models and/or types of sound transmitters 102 and sound receivers 104. The inverse filters may be used to compensate, for example variations in different acoustic transducer characteristics. Different sets of predetermined time increments can be provided from storage means 124 to parameter adjuster 120. Different inverse filters can be provided from storage means 124 to signal generator 122. It is contemplated that storage means 124 may be a memory, a magnetic disk, a database or a further storage means on a remote device, such as a device corresponding to the display 128.

Apparatus 100 may optionally include a display 128 for presenting, for example, the received signals x(t), x'(t), the received signal component s(t) at the skin surface, the estimated phase-inverted signal component $U_i(t)$, the predetermined time increment $\tau_i$, and an amplitude parameter A. The display 128 may further present control parameters for controlling the determination of the source sound pressure, for example, time increment variation, feature adjustment including amplitude adjustment, sound transmitter inverse filters, sound receiver inverse filters, and sets of predetermined time increment based on patient characteristics. It is contemplated that display 128 may include any display capable of presenting information including textual and/or graphical information.

Apparatus 100 may optionally include a control interface 126 for providing control parameters to the sound pressure determination system 106. Control interface 126 may further select signals to be displayed, for example on display 128. The control interface may include a pointing device type interface and/or a text interface for selecting control parameters, display parameters and/or storage parameters using display 128.

It is contemplated that apparatus 100 may be configured to connect to a global information network, e.g. the Internet, (not shown) such that the source sound pressure output may also be transmitted to a remote location for further processing and/or storage.

A suitable sound transmitter 102, sound receiver 104, sound pressure determination system 106, force actuator 108, force actuator 110, storage means 124, control interface 126, display 128 and control interface 130 for use with the present invention will be understood by one of skill in the art from the description herein.

Figure 2A:
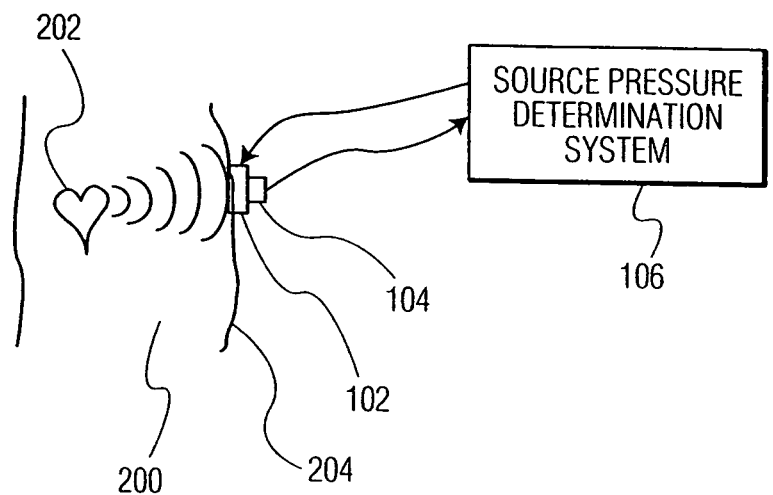
FIG. 2A is a cut-away side plan drawing illustrating coaxial placement of a sound receiver and a sound transmitter on a skin surface of a body according to an embodiment of the present invention.
Figure 2B:
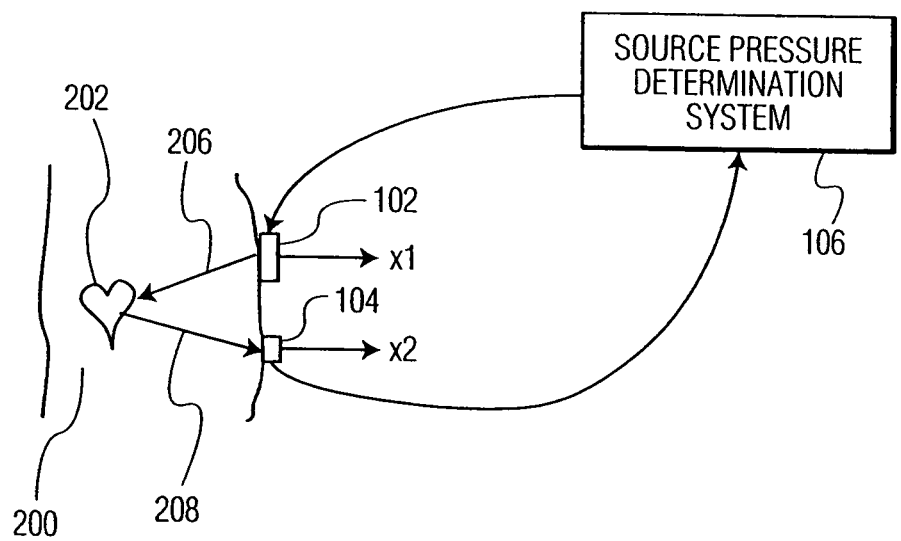
FIG. 2B is a cut-away side plan drawing illustrating the sound receiver and the sound transmitter located at different positions on the skin surface of the body according to an alternate embodiment of the present invention.

FIGS. 2A and 2B are cut-away side plan drawings illustrating alternative exemplary placement of sound transmitter 102 and sound receiver 104. More particularly, FIG. 2A is a cut-away side plan drawing illustrating a co-axial placement of sound transmitter 102 and sound receiver 104 on skin surface 204 of body 200; and FIG. 2B is a cut-away side plan drawing illustrating sound transmitter 102 and sound receiver 104 located at different positions on skin surface 204 of body 200.

Referring to FIG. 2A, according to an exemplary embodiment, sound transmitter 102 and sound receiver 104 may be coaxially positioned on the skin surface 204 of body 200. Both sound transmitter 102 and sound receiver 104 are desirably directed, with a same acoustic axis toward source 202.

Referring to FIG. 2B, in an alternate embodiment, sound transmitter 102 may be separated from sound receiver 104 such that sound transmitter 102 has optical axis x1 and sound receiver 104 has optical axis x2. In this embodiment, it is desirable that both sound transmitter 102 and sound receiver 104 are configured to be directed toward source 202, for example shown by path 206 and path 208, respectively. It is desirable, according to either coaxially positioned or separately located sound transmitter 102 and sound receiver 104, that sound transmitter 102 and sound receiver 104 be maintained in the same location throughout the procedure of estimating the source pressure proximate to the source, described herein.

Figure 3A:
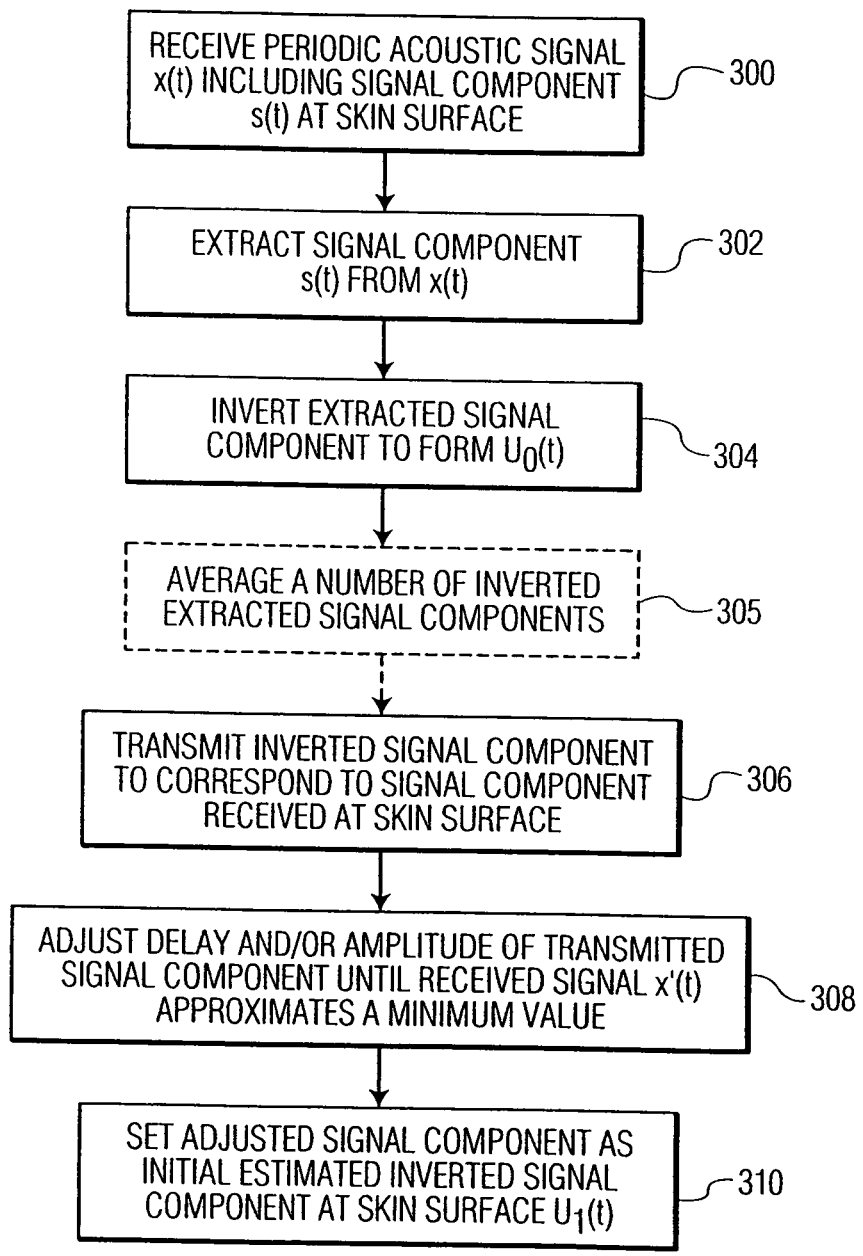
FIG. 3A is a flowchart illustrating an exemplary method for estimating an initial phase-inverted signal component at the skin surface according to an embodiment of the present invention.
Figure 3B:
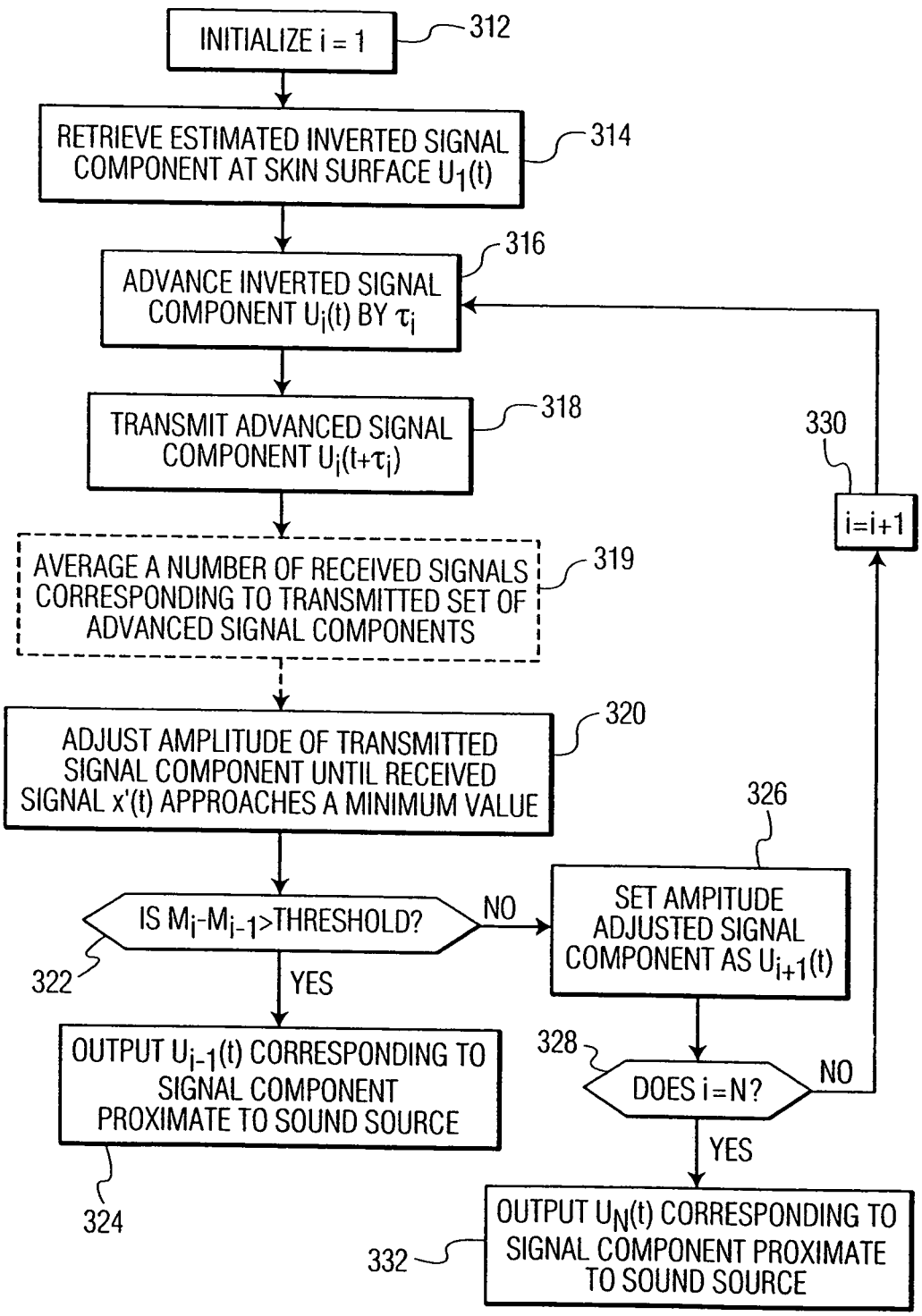
FIG. 3B is a flowchart illustrating an exemplary method for estimating a source sound pressure of the signal component proximate to the source according to an embodiment of the present invention.
Figure 4A:
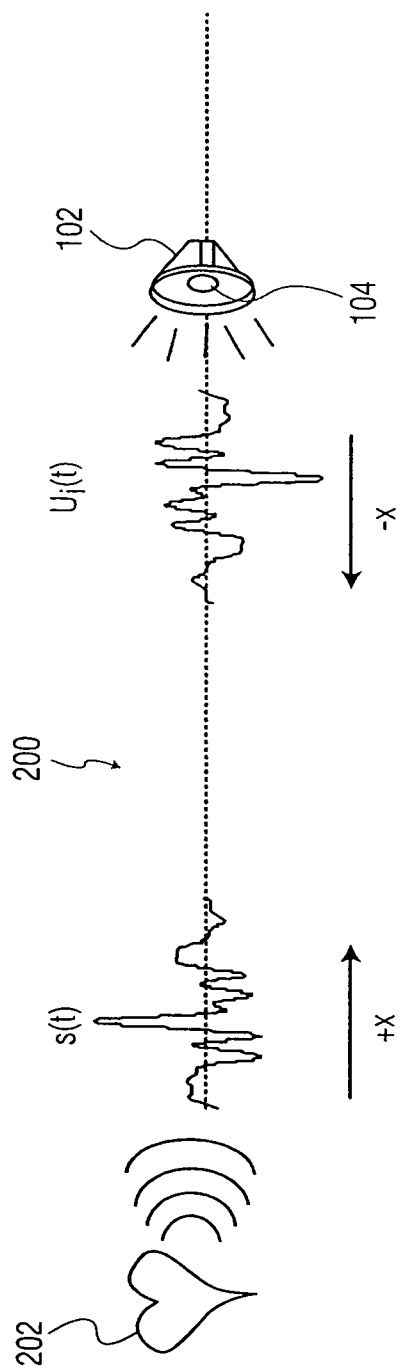
FIG. 4A is a signal propagation diagram that is useful for illustrating the transmission of an estimated phase-inverted signal component toward a signal component propagating within the body according to the exemplary method shown in FIGS. 3A and 3B.
Figure 4B:
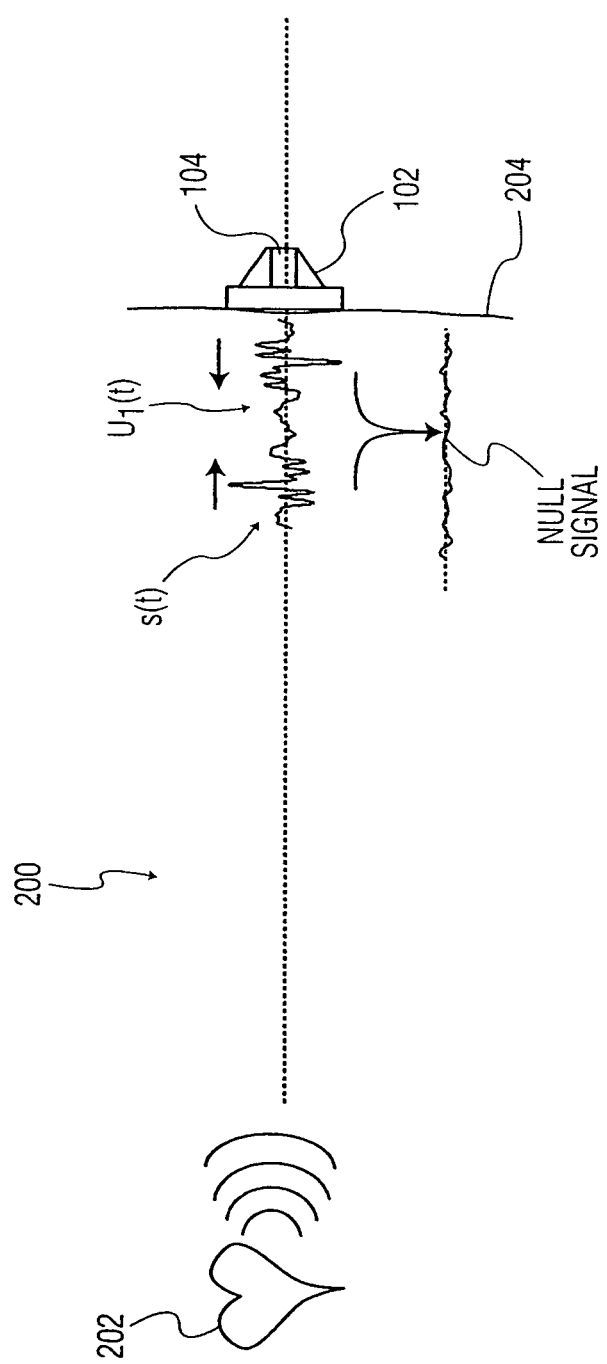
FIG. 4B is a signal propagation diagram that is useful for illustrating the reception of a null signal when the initial estimated phase-inverted signal component is transmitted to correspond to the signal component received at the skin surface according to the exemplary method shown in FIG. 3A.
Figure 4C:
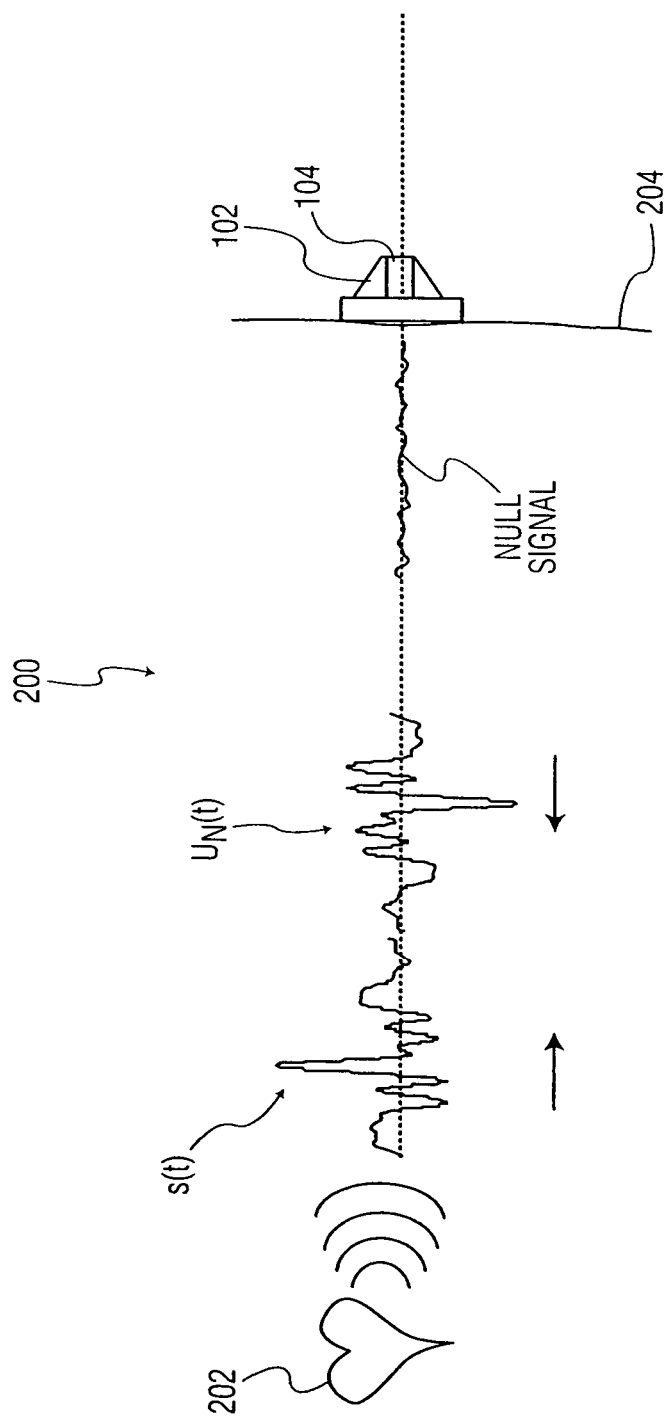
FIG. 4C is a signal propagation diagram that is useful for illustrating the reception of a null signal when the estimated phase-inverted signal component is transmitted to correspond to the signal component proximate to the source according to the exemplary method shown in FIG. 3B.

FIGS. 3A and 3B are flowcharts illustrating an exemplary method for noninvasively determining a source sound pressure according to an embodiment of the present invention. More particularly, FIG. 3A is a flowchart illustrating an exemplary method for estimating an initial phase-inverted signal component at the skin surface; FIG. 3B is a flowchart illustrating an exemplary method for estimating a source sound pressure of the signal component proximate to the source. The following figures illustrate signal flow diagrams useful for illustrating the exemplary method shown in FIGS. 3A and 3B: FIG. 4A illustrates the transmission of a phase-inverted signal component toward a signal component propagating within the body; FIG. 4B illustrates the reception of a null signal when an initial estimated phase-inverted signal component is transmitted to correspond to a signal component received at the skin surface; and FIG. 4C illustrates the reception of a null signal when an estimated phase-inverted signal component is transmitted to correspond to a signal component proximate to the source.

Referring to FIG. 4A, when a phase-inverted signal UN is transmitted from sound transmitter 102 into body 200, the phase-inverted signal will generally propagate in a -x direction toward source 202. At the same time, a signal component s(t) is transmitted from source 202 in the +x direction. At some location within body 200, the signal component s(t) will be combined with the phase-inverted signal $U_1(t)$ and, if the phase-inverted signal matches the signal component in shape, period and amplitude, a null signal will be produced, i.e. the phase-inverted signal will cancel the signal component.

According to an exemplary embodiment of the present invention, an amplitude of the signal component proximate to the source is reconstructed by first estimating the amplitude of the signal component received at the skin surface via transmission of the phase-inverted signal component. It is know to the skilled person that the propagation time of a sound within the transmission channel, body 200, is finite. It is also known that the amplitude of the signal component typically increases toward the source. Accordingly, an embodiment of the present invention advances the transmitted signal component, causing the transmitted signal component to combine with the signal component deeper within body 200 towards source 202. When the amplitude is adjusted to such that an approximate null signal is received, the amplitude of the signal component may be determined as being reconstructed at that location within the body. Accordingly, the process may continue to reconstruct the amplitude until the signal component is proximate to the source 202.

Referring to FIG. 3A, in step 300, a generally periodic acoustic signal x(t) including at least one signal component s(t) is received at skin surface 204, for example from sound receiver 104 (FIG. 1). In step 302 the desired signal component s(t) is extracted from the received signal x(t), for example by component extractor 114 (FIG. 1). In step 304, the extracted signal component s(t) is inverted in phase such that $U_0(t)=-s(t)$, for example by signal generator 122 (FIG. 1).

In step 306, the phase-inverted signal component $U_0(t)$ is transmitted, for example by sound transmitter 102 (FIG. 1) at the skin surface 204 to correspond to the signal component s(t) received at the skin surface 204. Accordingly, the received signal x'(t) is formed by the combination of s(t) at the skin surface 204 and the transmitted signal component $U_0(t)$. In step 308, a delay and/or an amplitude of the transmitted signal component may be adjusted until the received signal x'(t) approximates a minimum value. For example a delay and/or amplitude may be provided to signal generator 122 from parameter adjuster 120, responsive to controller 118 and based on the value provided by null signal estimator 116 (FIG. 1).

In step 310, the adjusted signal component determined in step 308 is set as the initial estimated inverted signal component at skin surface 204, $U_1(t)$. Referring to FIG. 4B, $U_1(t)$ is the phase-inverted signal component adjusted as in step 308 such that the amplitude and delay of $U_1(t)$ correspond to the signal component s(t) that is received at the surface. Accordingly, $U_1(t)$ and $s(t)$ will combine, at the skin surface 204, to form a null signal, i.e. the transmitted signal component $U_1(t)$ and $s(t)$ will substantially cancel at the skin surface 204.

Referring back to FIG. 3A, it is contemplated that the signal component may be extracted from a number of signals in step 302, for example, by component extractor 114, and inverted in step 304. In optional step 305, the number of inverted extracted signal components may be averaged in order to reduce instantaneous variations in amplitude of the signal components, for example, due to respiration or background noise.

Referring to FIG. 3B, in step 312, the index i is initialized and in step 314, $U_1(t)$, the initial estimated phase-inverted signal component at the skin surface, is retrieved.

In step 316, the phase-inverted signal $U_i(t)$ is advanced by predetermined time increment $\tau_i$, i.e. $U_i(t+\tau_i)$, for example, parameter adjuster 120 may provide $\tau_i$ to signal generator 122 responsive to controller 118 (FIG. 1). In step 318, the advanced signal is transmitted, for example by sound transmitter 102. In step 320, the amplitude of the transmitted signal component is adjusted until the received signal $x'(t)$ approximates a minimum value. For example, an amplitude may be provided to signal generator 122 from parameter adjuster 120, responsive to controller 118 based on the value provided by null signal estimator 116 (FIG. 1).

In step 322, it is determined whether a difference between a minimum value at index i ($M_i$) and the minimum value at index i−1 ($M_{i-1}$) is greater than a predetermined threshold. If the phase-inverted signal component is advanced to a point beyond the source at index i, the phase-inverted signal $U_i(t)$ will no longer substantially cancel the signal component $s(t)$ and thus $M_i$ will be greater than $M_{i-1}$. In this case, $U_{i-1}(t)$ may be selected as being proximate to the source. In an exemplary embodiment, the difference $M_i-M_{i-1}$ may be compared to a predetermined threshold. If $M_i-M_{i-1}$ is greater than the predetermined threshold, step 322 proceeds to step 324. In step 324, estimated phase-inverted signal component $U_{i-1}(t)$ is output and the process is complete. The amplitude of signal $U_{i-1}(t)$ may be used to determine the signal component proximate to the source.

If $M_i-M_{i-1}$ is not greater than the predetermined threshold, step 322 proceeds to step 326. In step 326, the amplitude adjusted signal is set as the estimated signal component $U_{i+1}(t)$ at a location within the body corresponding to time increment $\tau_i$.

In step 328, it is determined whether the limit N is reached. If the time increment i is not equal to N, step 328 proceeds to step 330. In step 330, the index is updated and step 330 proceeds to step 316. Steps 316-320 are repeated until the predetermined threshold is reached or steps 316-326 are repeated until the time increment is equal to N.

If the time increment i is equal to N, step 328 proceeds to step 332. In step 332, estimated phase-inverted signal component $U_N(t)$ is output and the process is complete. The amplitude of signal $U_N(t)$ may be used to determine the signal component proximate to the source.

It is contemplated that, in step 318, a set of transmitted signal components may be transmitted to combine with a respective number of signal components advanced by time increment $\tau_i$. These transmitted signal components desirably each have the same amplitude. In optional step 319, a corresponding number of received signals $x'(t)$ may be averaged in order to reduce instantaneous variations in the amplitude of the propagating signal components, for example, due to respiration or background noise. Accordingly, in step 320, the amplitude of the set of transmitted signals may be adjusted until the averaged received signal approximates a minimum value.

It is contemplated that each $U_i(t)$ and its corresponding $M_i$ determined in step 320 may be stored, for example, in storage means 124 up to the limit N, for example, to form U=$[U_1(t) \ldots U_N(t)]$ and M=$[M_1 \ldots M_N]$. A minimum may be determined from among the stored M values within a range that corresponds to an estimated position of the source. The corresponding index and thus the corresponding $U_i(t)$ may used to determine the signal component proximate to the source.

Referring to FIG. 4C, $U_N(t)$ is the phase-inverted signal component adjusted as in step 320 such that the amplitude corresponds to the signal component $s(t)$ proximate to source 202. Accordingly, $U_N(t)$ and $s(t)$ will combine, proximate to source 202, to form a null signal, i.e. the transmitted signal component and $s(t)$ will cancel proximate to source 202.

It is contemplated that the phase-inverted signal component $U_1(t)$ at the skin surface and the phase-inverted signal component $U_N(t)$ proximate to the source may be used to estimate the transmission channel. An inverse filter of the estimated transmission channel may be determined and used to better approximate the signal component amplitude proximate to the source. It is contemplated that any known-in-the art methods may be used to estimate the transmission channel and to provide an inverse filter for the transmission channel. As is known to the skilled person, the inverse filter may be combined with the $U_N(t)$ proximate to the source, for example, by convolution in the time domain or multiplication in the frequency domain, in order to substantially remove the characteristics of the transmission channel.

Although the invention has been described in terms of apparatus and methods for noninvasively determining a sound pressure of a source located within a body, it is contemplated that one or more components may be implemented in software on microprocessors/general purpose computers (not shown). In this embodiment, one or more of the functions of the various components may be implemented in software that controls a general purpose computer. This software may be embodied in a computer readable carrier, for example, a magnetic or optical disk, a memory-card or an audio frequency, radio-frequency, or optical carrier wave.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A system for noninvasively determining a source sound pressure of a source located inside of a body, the source transmitting a generally periodic acoustic signal including at least one signal component to a surface of the body, the system comprising:

means for receiving the signal component at the surface of the body;

means for estimating an initial phase-inverted signal component responsive to the signal component received at the surface, the phase-inverted signal component approximating a phase-inverted version of the received signal component;

means for transmitting the phase-inverted signal component advanced by a predetermined time increment toward the source via the surface, the predetermined time increment corresponding to a distance of the signal component within the body;

means for adjusting at least one feature of the transmitted signal component until a further received signal approximates a minimum value;

means for setting the adjusted signal component as the phase-inverted signal component corresponding to the signal component at the distance, whereby the system determines the phase-inverted signal component that corresponds to the signal component being proximate to the source.

2. Apparatus for noninvasively determining a source sound pressure of a source located inside of a body, the source transmitting a generally periodic acoustic signal including at least one signal component to a surface of the body, the system comprising:

a first acoustic transducer disposed on the surface for receiving the signal component at the surface of the body;

a second acoustic transducer disposed on the surface of the body; and a source pressure determination system comprising:
  a signal generator configured to generate an estimated phase-inverted signal component responsive to the signal component received at the surface by the first acoustic transducer, the phase-inverted signal component approximating a phase-inverted version of the received signal component, and
  a controller for:
    a) providing a predetermined time increment to the signal generator for advancing the generated phase-inverted signal component, the predetermined time increment corresponding to a distance of the signal component within the body, the second acoustic transducer transmitting the advanced phase-inverted signal component provided by the signal generator toward the source, and
    b) adjusting at least one feature of the estimated phase-inverted signal generated by the signal generator until a further signal received from the first acoustic transducer approximates a minimum value, the controller setting the adjusted signal component as the phase-inverted signal component corresponding to the signal component at the distance, wherein the source pressure determination system determines the phase-inverted signal component that corresponds to the signal component being proximate to the source.

3. Apparatus according to claim 2, the source pressure determination system further comprising:

a null signal estimator configured to receive the further received signal from the first acoustic transducer, the null signal estimator determining the approximate minimum value from the further received signal and providing the approximate minimum value to the controller; and a parameter adjuster configured to provide the predetermined time increment and an amplitude parameter to the signal generator responsive to the controller.

4. Apparatus according to claim 2, the source pressure determination system further comprising a component extractor for receiving the generally periodic acoustic signal from the first acoustic transducer and extracting the at least one signal component from the generally periodic acoustic signal, wherein the signal generator estimates the phase-inverted signal component responsive to the extracted signal component received from the component extractor.

5. Apparatus according to claim 2, wherein the first acoustic transducer and the second acoustic transducer are coaxially located on the surface.

6. Apparatus according to claim 2, wherein the first acoustic transducer is at a location different from the second acoustic transducer, the first acoustic transducer and the second acoustic transducer each being directed toward the source.

7. Apparatus according to claim 2, the apparatus further comprising a force actuator between the surface and the first acoustic transducer, the force actuator configured to detect an applied pressure by the first acoustic transducer on the surface.

8. Apparatus according to claim 2, the apparatus further comprising a force actuator between the surface and the second acoustic transducer, the force actuator configured to detect an applied pressure by the second acoustic transducer on the surface.

9. Apparatus according to claim 2, the apparatus further comprising a display coupled to source pressure determination system for presenting at least one of the further received signal, the received signal component, the estimated phase-inverted signal component, the predetermined time increment and an amplitude parameter for adjusting the amplitude of the transmitted signal.

10. Apparatus according to claim 2, the apparatus further comprising a control interface coupled to source pressure determination system for providing control parameters to the source pressure determination system.

* * * * *